(12) United States Patent
Mukhopadhyay et al.

(10) Patent No.: US 8,395,000 B2
(45) Date of Patent: Mar. 12, 2013

(54) METHOD FOR PRODUCING FLUORINATED ORGANIC COMPOUNDS

(75) Inventors: Sudip Mukhopadhyay, Williamsville, NY (US); Haridasan K. Nair, Williamsville, NY (US); Hsueh S. Tung, Getzville, NY (US); Michael Van Der Puy, Amherst, NY (US); Daniel C. Merkel, West Seneca, NY (US); Rajesh K. Dubey, Buffalo, NY (US); Jing Ji Ma, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 347 days.

(21) Appl. No.: 12/702,135

(22) Filed: Feb. 8, 2010

(65) Prior Publication Data

US 2010/0210883 A1 Aug. 19, 2010

Related U.S. Application Data

(63) Continuation of application No. 11/592,761, filed on Nov. 3, 2006, now Pat. No. 7,674,939, and a continuation-in-part of application No. 11/118,503, filed on Apr. 29, 2005, now Pat. No. 7,345,209, and a continuation-in-part of application No. 11/118,504, (Continued)

(51) Int. Cl.
C07C 17/25 (2006.01)
C07C 21/185 (2006.01)
C07C 21/18 (2006.01)

(52) U.S. Cl. .................. 570/155; 570/156; 570/136

(58) Field of Classification Search .................. None
See application file for complete search history.

(56) References Cited

U.S. PATENT DOCUMENTS

| | | | |
|---|---|---|---|
| 2,931,840 A | 4/1960 | Marquis | |
| 2,996,555 A | 8/1961 | Rausch et al. | |
| 3,472,826 A | 10/1969 | Potts et al. | |
| 3,659,023 A | 4/1972 | Regan | |
| 4,086,407 A | 4/1978 | Fozzard | |
| 4,650,914 A | 3/1987 | Woodard | |
| 4,798,818 A | 1/1989 | Baizer et al. | |
| 4,900,874 A | 2/1990 | Ihara et al. | |
| 5,162,594 A | 11/1992 | Krespan | |
| 5,532,419 A | 7/1996 | Van Der Puy et al. | |
| 5,545,777 A | 8/1996 | Morikawa et al. | |
| 5,574,192 A | 11/1996 | Van Der Puy et al. | |
| 5,679,875 A | 10/1997 | Aoyama et al. | |
| 5,710,382 A | 1/1998 | Dunmead et al. | |
| 5,969,198 A | 10/1999 | Thenappan et al. | |
| 5,986,151 A | 11/1999 | Van Der Puy | |
| 6,023,004 A | 2/2000 | Thenappen et al. | |
| 6,066,769 A | 5/2000 | Nappa et al. | |
| 6,111,150 A | 8/2000 | Sakyu et al. | |
| 6,124,510 A | 9/2000 | Elsheikh et al. | |
| 6,369,284 B1 | 4/2002 | Nappa et al. | |
| 6,548,719 B1 | 4/2003 | Nair et al. | |
| 6,809,226 B1 | 10/2004 | Pennetreau et al. | |
| 6,958,424 B1 | 10/2005 | Nair et al. | |
| 6,977,316 B1 | 12/2005 | Mukhopadhyay et al. | |
| 7,026,520 B1 | 4/2006 | Mukhopadhyay et al. | |
| 7,026,521 B1 | 4/2006 | Mukhopadhyay et al. | |
| 7,071,367 B1 | 7/2006 | Mukhopadhyay et al. | |
| 7,132,578 B1 | 11/2006 | Mukhopadhyay et al. | |
| 7,135,601 B2 | 11/2006 | Mukhopadhyay et al. | |
| 7,189,884 B2 | 3/2007 | Mukhopadhyay et al. | |
| 7,196,236 B2 | 3/2007 | Mukhopadhyay et al. | |
| 2003/0060670 A1 | 3/2003 | Nair et al. | |
| 2004/0119047 A1 | 6/2004 | Singh et al. | |
| 2005/0020862 A1 | 1/2005 | Tung et al. | |
| 2005/0080302 A1 | 4/2005 | Baker et al. | |
| 2005/0090698 A1 | 4/2005 | Merkel et al. | |
| 2005/0171391 A1 | 8/2005 | Janssens et al. | |
| 2007/0112227 A1 | 5/2007 | Mukhopadhyay et al. | |
| 2007/0112228 A1 | 5/2007 | Mukhopadhyay et al. | |
| 2007/0112229 A1 | 5/2007 | Mukhopadhyay et al. | |
| 2007/0112230 A1 | 5/2007 | Mukhopadhyay et al. | |
| 2007/0129580 A1 | 6/2007 | Mukhopadhyay et al. | |

FOREIGN PATENT DOCUMENTS

| | | |
|---|---|---|
| EP | 0522639 | 1/1993 |
| EP | 0644173 | 3/1995 |
| EP | 974571 A2 | 1/2000 |
| GB | 844597 | 8/1960 |
| JP | 11140002 | 5/1999 |
| JP | 2000169404 | 6/2000 |
| JP | 2000178543 | 6/2000 |
| WO | 9008752 | 8/1990 |
| WO | 9504021 | 2/1995 |
| WO | 96/01797 A | 1/1996 |
| WO | 98/42645 | 3/1998 |
| WO | 98/21171 | 5/1998 |
| WO | 99/48993 | 9/1999 |
| WO | 00/39242 | 7/2000 |
| WO | 01/07384 | 2/2001 |
| WO | 03027051 | 4/2003 |
| WO | 2005/012212 | 2/2005 |
| WO | 2005/042451 A | 5/2005 |

(Continued)

OTHER PUBLICATIONS

Rozen et al. Journal of Organic Chemistry 1986, 51, 3607-3611.*

(Continued)

*Primary Examiner* — Yevegeny Valenrod
(74) *Attorney, Agent, or Firm* — Bruce O. Bradford

(57) ABSTRACT

Disclosed are methods for producing fluorinated organic compounds, including hydrofluoropropenes, which preferably comprises converting at least one compound of formula (I):

$$CF_3CHXCH_2X \quad (I)$$

to at least one compound of formula (II)

$$CF_3CZCHZ \quad (II).$$

where X is independently Cl, Br, I or F, and Z independently is H or F. In certain preferred embodiments, each Z is different.

24 Claims, No Drawings

Related U.S. Application Data filed on Apr. 29, 2005, now Pat. No. 7,371,904, and a continuation-in-part of application No. 11/118,530, filed on Apr. 29, 2005, now Pat. No. 7,189,884.

(60) Provisional application No. 60/733,355, filed on Nov. 3, 2005, provisional application No. 60/567,427, filed on Apr. 29, 2004, provisional application No. 60/567,425, filed on Apr. 29, 2004, provisional application No. 60/567,426, filed on Apr. 29, 2004, provisional application No. 60/567,429, filed on Apr. 29, 2004, provisional application No. 60/567,428, filed on Apr. 29, 2004.

(56) References Cited

FOREIGN PATENT DOCUMENTS

| WO | 2005108332 | 11/2005 |
|----|-----------|---------|
| WO | 2005108334 | 11/2005 |
| WO | 2007019355 A | 2/2007 |

OTHER PUBLICATIONS

Banks, et al., Journal of Fluorine Chemistry, vol. 82, Issue 2, pp. 171-174 (1997).
Database Beilstein, Beilstein Institute for Organic Chemistry, M. Van Der Puy: J. Fluorine Chemistry, vol. 81, No. 2, 1997, pp. 187-192 XP002424669.
Database Beilstein, Beilstein Institute for Organic Chemistry, Haszeldine, Steele: J. Chem. Soc. 1953, p. 1592, 1597, XP0022424670.
Database WPI Week 199812, AN 1998-126110, XP002427152, Derwent Publications Ltd., London, GB & JP 10 007605A (Central Glass Co LTD) Jan. 13, 1998 abstract.
Dickson, R.S., Fluorcarbon-Aluminium Compounds, Aust. J. Chem., 1972, 25, 761-8.
Haszeldine R.N., Free-radical Additions to Unsaturated Systems. Part XVII.[1] Reaction of Trifluoroiodomethane with Mixtures of Ethylene and Vinyl Fluoride and of Ethylene and Propene, Journal of Chemical Society, Section C: (3), 414-21. p. 415.
Henne, Albert L., et al., Chlorinated Derivatives of 2-Floropropane[1] J. American Chemical Society, Jul. 11, 1941: pp. 2692-2694, vol. 63.
J Burdon et al.: J. Fluorine Chemistry, vol. 40, pp. 283-318, XP002424668.
March, J. Advanced Organic Chemistry, 1997, pp. 631-636, McGraw-Hill International Book Company, XP002427150.
Vittorio Minanari, A Novel Systensis of Perhalogenated Alkenes, J. Org. Chem. 1992, 57, 5018-5019.
Kunyants et al, "Reaction of Fluoroolefins Communication," 1960, pp. 1312-1317, XP000578879.
Kunshenko BV et al., Reaction of Organic Compounds With SF4-HF-Hallogenating System VII, 1992, XP002344564.
Database Beilstein, XP002426121.
Gambareto et al., "The Reactions of Chlorine Monofluoride With Unsaturated Compounds," 1976, XP002426119.
Zhurani Organicheskol Khimii 28(4), 672-80 (1982).
XP000578879, Bulletin of the Academy of Sciences of the USSR, Division of Chemical Sciences, ISSN 0568-5230, p. 1312-1317.
Salmon, R.P. et al., Chemical and Physical Processes in Combustion, Vilanova University 1996, pp. 507-510, XP001120412 US.

* cited by examiner

METHOD FOR PRODUCING FLUORINATED ORGANIC COMPOUNDS

CROSS-REFERENCES TO RELATED APPLICATIONS

This application is a Continuation of U.S. patent application Ser. No. 11/592,761, (now U.S. Pat. No. 7,674,939) filed on Nov. 3, 2006, which claims the priority benefit of U.S. Provisional Patent Application No. 60/733,355 filed Nov. 3, 2005 and is a Continuation-in-Part of U.S. patent application Ser. No. 11/118,503, (now U.S. Pat. No. 7,345,209) filed on Apr. 29, 2005, which in turn claims the priority benefit of U.S. Provisional Patent Application Nos. 60/567,427 and 60/567,425 filed Apr. 29, 2004.

This application is also a Continuation-in-Part of U.S. patent application Ser. No. 11/118,504, (now U.S. Pat. No. 7,371,904) filed on Apr. 29, 2005, which in turn claims the priority benefit of U.S. Provisional Patent Application Nos. 60/576,426 and 60/567,429 filed Apr. 29, 2004.

This application is also a Continuation-in-Part of U.S. patent application Ser. No. 11/118,530, (now U.S. Pat. No. 7,189,884) filed on Apr. 29, 2005, which in turn claims the priority benefit of U.S. Provisional Patent Application No. 60/567,428 filed Apr. 29, 2004.

The disclosures of each of the above-mentioned applications are incorporated herein by reference. Also incorporated herein by reference are U.S. Provisional Patent Application Nos. 60/733,378; 60/733,444; 60/733,383; 60/733,377 and 60/733,379, each of which was filed on Nov. 3, 2005.

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts, including a sizeable amount of carbon black. The carbon black is not only unwanted, it tends to deactivate the catalyst used in the process.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding prior teachings applicants appreciate a continuing need for methods of efficiently preparing certain hydrofluorocarbons, particularly tetrafluorpropenes such as HFO-1234yf and HFO-1234ze (including cis- and trans-forms thereof).

SUMMARY OF THE INVENTION

Applicants have developed a method for producing fluorinated organic compounds, including hydrofluoropropenes, which preferably comprises converting at least one compound of formula (I):

$$CF_3CHXCH_2X \qquad (I)$$

to at least one compound of formula (II)

$$CF_3CZCHZ \qquad (II),$$

where X is independently Cl or F, and Z independently is H or F. In certain preferred embodiments, each Z is different.

The preferred converting step of the present invention comprises dehydrohalogenating at least one compound of formula (I). The dehydrohalogenation step comprises in preferred embodiments introducing said at least one compound of formula (I) to a reaction system under conditions effective to convert, and preferably convert at least about 50%, and even more preferably at least about 70%, of said compound of formula (I). It is also generally preferred that said reaction step produces a reaction product having at least about 70% selectivity, and even more preferably at least about 80% selectivity, to compounds of formula (II). In certain highly preferred embodiments, the reaction step produces a reaction product having at least about 70% selectivity, and even more preferably at least about 80% selectivity, to, tetrafluoropropene, and even more preferably HFO-1234yf and/or HFO-1234ze.

In certain preferred embodiments, the converting step comprises reacting a compound of formula (I) in the gas phase, in the liquid phase, or a combination of these, with gas phase reactions preferably occurring in the presence of catalyst.

DETAILED DESCRIPTION OF PREFERRED EMBODIMENTS

One beneficial aspect of the present invention is that it enables the production of desirable fluroolefins, preferably C3 fluoroolefins, from relatively attractive starting materials, and in preferred embodiments the present methods are capable of achieving very desirable levels of conversion of the starting materials while also providing high levels of selectivity to the desired products. Flouropropenes in general, and trifluoropropenes in particular are in many embodiments an advantageous starting material because such products are relatively inexpensive, are relatively easy to handle, and are generally readily available in commercial quantities or can be easily produced from other readily available materials. For example trifluorpropene can be synthesized by the Cu-catalyzed liquid-phase coupling of CCl$_4$ and CH$_2$=CH$_2$, preferably followed by hydrofluorination.

Thus, in certain embodiments the present methods include the step of reacting fluorinated olefin, more preferably a fluorinated olefin having three carbon atoms, such as trifluoropropene, with a halogen addition agent, preferably a chlorine addition agent and/or a fluorine addition agent, under conditions effective to produce a compound of formula (I)

$$CF_3CHXCH_2X \quad (I)$$

where X is independently Cl or F. In preferred embodiments, the fluorinated olefin reactant is a compound of formula (III)

$$CX_nY_{3-n}CY=CH_mY_{2-m} \quad (III)$$

where each X is independently Cl or F, each Y is independently H, Cl or F, n is 1, 2 or 3, and m is 1 or 2. In preferred embodiments, the compound of formula (III) comprises, and even more preferably consists essentially of CF$_3$CH=CH$_2$.

The reaction by which the compound of formula (III) is converted to a compound of formula (I) is sometimes referred to herein for convenience, but not necessarily by way of limitation, as a halogen addition reaction.

Preferably the formula (I) compound, which is preferably formed by a process comprising a halogen addition reaction, is then exposed to reaction conditions, which are sometimes referred to herein for convenience, but not necessarily by way of limitation, as a dehydrohalogenation reaction, to produce a reaction product containing one or more of the desired fluoroolefins, preferably one or more compounds of formula (II). Preferred aspects of each of the preferred steps is described below, with the titles used as headings for these steps being used for convenience but not necessarily by way of limitation.

I. Halogen Addition

In preferred embodiments, the reactant compound of formula (III) is fluorinated olefin, more preferably fluorinated propylene and even more preferably CF$_3$CH=CH$_2$ (sometimes referred to herein as the "compound of formula (IIIA)"). It is further preferred that the halogen addition agent is a compound of formula X$_m$Y$_{2-m}$ where X, Y and m are as described above. Preferably, the halogen addition agent is one or more of ClF, Cl$_2$, F$_2$ and HF.

For embodiments directed primarily to the production of CF$_3$CF=CH$_2$ (HFO-1234yf), it is generally preferred that the compound of formula (I) comprise a compound of formula (IA)

$$CF_3CHFCH_2F \quad (IA),$$

that is, a compound in which X is F (HFC-245eb). In many preferred embodiments, HFC-245eb is produced by a halogen addition reaction involving trifluoropropene and a halogen addition agent comprising, and preferably consisting essentially of, F$_2$.

For embodiments directed primarily to the production of CF$_3$CH=CHF (HFO-1234ze), it is generally preferred that the compound of formula (I) comprise a compound of formula (IB)

$$CF_3CHClCH_2F \quad (IB).$$

In many preferred embodiments, the compound of formula (IB) is produced by a halogen addition reaction involving trifluoropropene and a halogen addition agent comprising, and preferably consisting essentially of, ClF.

In certain preferred embodiments, the halogen addition step comprises contacting, (preferably by introducing into a reactor) the compounds in an X$_m$Y$_{2-m}$:formula (III) mole ratio of from about 0.01:1 to about 50:1, and even more preferably of from about 0.1:1 to about 10:1. In preferred embodiments in which the compound of X$_m$Y$_{2-m}$ comprises F$_2$ and the formula III compound comprises CF$_3$CH=CH2, the F$_2$:trifluoropropene mole ratio of the feeds to the reactor are from about 0.01:1 to about 10:1 and even more preferably from about 0.1:1 to about 1:1. In preferred embodiments in which the compound of X$_m$Y$_{2-m}$ comprises ClF and the formula III compound comprises CF$_3$CH=CH$_2$, the ClF:trifluoropropene mole ratio of the feeds to the reactor are from about 0.01:1 to about 10:1 and even more preferably from about 0.1:1 to about 2:1.

This reaction step can be carried out in the liquid phase or in the gas phase, and it is contemplated that the reaction can be carried out batch wise, continuous, or a combination of these.

A. Preferred Liquid Phase Reactions

Certain preferred embodiments of this reaction (particularly when the halogenation agent (the X$_m$Y$_{2-m}$ compound) is ClF, HF or Cl$_2$, or combinations of two or more of these) involve relatively low temperature reactions in which at least the organic reactant(s) are charged to the reactor as liquids, with the reactor preferably maintained at least during a portion of the reaction at a temperature of from about −90° C. to about −18° C., and at least a portion of the reaction is carried in the liquid phase (the normal boiling point of the preferred reactant trifluoropropylene is −18° C.). However, it is contemplated that at least some portion of the reaction product may be produced and/or removed from the reaction mixture in such embodiments as a gaseous material. For example, it is preferred in certain embodiments to charge a reaction vessel, such as a stirred tank reactor, with the compound of formula (III), preferably formula (IIIA), so as to bring the contents of the reactor to a temperature of from about −80° C. to about −60° C., and to then add ClF to the reaction vessel. Preferably the reaction mixture has kinetic energy added to provide a substantially uniform reaction mixture (such as stirring) for a time of from about 0.1 hour to about 1 hour at a temperature of from about −60° C. to about −50° C. The temperature of the reaction mixture is then preferably raised to a temperature of about −20° C. for a period of from about 0.5 hour to about 5 hour, preferably for about 3 hours, under vigorous stifling. The reaction mixture is then preferably cooled to a temperature of from about −60° C. to about −40° C. (preferably about −50° C.) and water is added to the reactor at subzero temperature to neutralize the mineral acids such as HF and HCl formed during the reaction and reaction mixture is stirred for a period of from about 0.1 to about 0.5 hours. Water addition reaction is highly exothermic, thus, addition of water at around 0° C. to −30° C. is preferred to keep the exothermicity under control. The reactor temperature is then preferably raised to from about 10° C. to about 30° C., preferably 20° C., and the gaseous products from the reactor are then preferably removed and transferred to a collection vessel.

For those preferred embodiments which utilize ClF as a reactant, it is sometimes preferred to provide source of chlorine and fluorine by the liquid-phase reaction of HF and Cl$_2$ in the presence of catalyst, preferably a transition metal catalyst, and even more preferably a transition metal halide catalysts such as FeCl$_3$, SnCl4, TaCl$_5$, TiCl$_4$, SbCl$_5$, SbCl$_3$, and CrCl$_3$, SbF$_3$, SbF$_5$, AlF$_3$, and CrF$_3$, and combinations of two or more of these. In certain preferred embodiments, therefore, the present step comprises contacting CF$_3$CH=CH2, HF and Cl$_2$ in the presence of a metal catalyst, preferably a metal chloride salt, preferably with addition of kinetic energy to provide a substantially uniform reaction mixture (such as stirring), under conditions effective to form a reaction product comprising the desired compound of formula I. In certain preferred embodiments, the reaction is carried out, preferably at a temperature of from about −90° C. to about −20° C., more preferably from about −50° C. to about −30° C., under conditions effective to achieve a percentage conversion of at least about 30%, more preferably at least about 70%, and even more preferably at least about 100% of the compound of formula III. Preferably, the reaction conditions are effective to achieve a percentage selectivity to compounds of formula I, and preferably compounds of formula (IA) of at least about 30%, more preferably at least about 50% to at least about 75%, and even more preferably at least about 95%. In certain preferred embodiments a selectivity of about 98% or greater is achieved.

As used herein, the term "percentage conversion" with respect to a reactant, which typically is a limiting agent, refers to the moles reacted in the reaction process divided by the moles of that limiting reactant in the feed to the process multiplied by 100.

As used herein, the term "percentage selectivity" with respect to an organic reaction product refers to the ratio of the moles of that reaction product to the total of the organic reaction products multiplied by 100.

In certain preferred embodiments the reaction time for the preferred liquid phase reaction is from about 0.1 to about 3 hours. The reaction product in preferred embodiments in which ClF is the halogen addition agent includes one or more of $CF_3CHClCH_2F$, $CF_3CHClCH_2Cl$, $CF_3CHFCH_2Cl$, $CF_3CH_2CH_2F$ and/or $CF_3CH_2CH_2Cl$. In preferred embodiments, the reaction product comprises from about 40 wt. % to about 60 wt. % $CF_3CHClCH_2F$, from about 10 to about 30 wt. % $CF_3CHClCH_2Cl$, from about 5 to about 15 wt % $CF_3CHFCH_2Cl$, from about 5 to about 10 wt % $CF_3CH_2CH_2F$, and about 3 to about 8 wt % $CF_3CH_2CH_2Cl$.

It will be appreciated that many alternatives for the provision of ClF in accordance with this preferred step of the present invention are available and within the scope hereof. By way of example, the reactant ClF may be provided in certain embodiments simply by purchasing the needed quantity of the material in the appropriate form. In other preferred embodiments, it is desirable to provide the chlorine and fluorine conducting a liquid-phase reaction of HF and Cl2, preferably in the presence of transition metal halide such as $SbF_5$, as described above or using similar reactions. Such reactions, especially single stage reactions, can be achieved using any equipment and conditions known and available in the art for such type of reaction, preferably at a temperature of from about −20° C. to about −90° C., and even more preferably the reaction temperature is maintained at a temperature of from about −20° C. to about −50° C.

As an alternative to the above mentioned single stage process, in certain embodiments a two stage scheme is used in which the reaction of HF and $Cl_2$ is carried out in a first vessel, stage or the like, and then in a second vessel, stage or the like the compound of formula (III) is added to initiate the halogen addition reaction to form the compound of formula (I). In such embodiments, it is generally preferred that the first stage is a liquid phase reaction and the second stage is also a liquid phase reaction. In such embodiments it is found that the conversion can be improved, preferably to at least about 80%.

B. Preferred Gas/Liquid Phase Reactions

The formation of a compound of formula I, particularly a compound of formula (IB) ($CF_3CHFCH_2F$) may also be carried out at least partially in a liquid phase reaction using $F_2$ as the halogen addition agent where the $F_2$ is introduced to the reaction mixture as a gas. For the purpose of convenience, but not by way of limitation, such a reaction arrangement is sometimes referred to herein as a gas/liquid phase reaction. Thus, for certain preferred embodiments, particularly those preferred embodiments which utilize $F_2$ as a reactant, it is preferred to provide a compound of formula (I) by a reaction which is conducted primarily in the liquid phase but in which the $F_2$ reactant is introduced in the gas phase. In such embodiments HF is preferably used as a solvent (preferably an inert solvent) for the reaction and a catalyst is not required. In certain of such preferred embodiments the $F_2$ is provided in diluted form, preferably blended with an inert gas, such as nitrogen, in amount of about 5-100% (preferably about 10%) of the total of $F_2$ and inert gas. The gas is preferably contacted with the compound of formula (III), preferably in some cases by bubbling the gas through the liquid in a stirred tank reactor at a temperature of from about −20° C. to about −55° C. for a time of from about 0.5 to about 1.5 hours. Preferred reactor pressure is from about 15 to about 80 psia, and even more preferably from about 20 to about 70 psia. In such embodiments the conversion of the formula III compound, particularly formula (IIIA) compounds, is preferably at least about 80 to about 100%, more preferably at least about 40 to about 60%, and selectivity to compounds of formula (I) is preferably at least about 30%, more preferably at least about 35%, and even more preferably at least about 40%.

C. Preferred Gas Phase Reactions

For certain preferred embodiments, particularly those preferred embodiments which utilize $F_2$ as a halogen addition agent, it is preferred to provide a compound of formula (I) by a gas-phase reaction. In such preferred embodiments, the compound of formula (III) and the halogen addition agent are introduced into and appropriate reaction vessel in the form of a gas and the reactor is preferably maintained at a temperature of from about −18° C. for a time of from about 5 minutes to about 16 hours, and the reaction products are produced mainly as liquids which separate from the gaseous reactants in the vessel. Preferred reactor pressure is atmospheric. In such embodiments the conversion of the formula III compound, particularly formula (IIIA) compounds, is preferably at least about 5%, more preferably at least about 10%, and selectivity to compounds of formula (I) is preferably at least about 30%, more preferably at least about 35%, and even more preferably at least about 50%.

II. Formation of the Compound of Formula II

The methods of the present invention preferably comprise contacting a compound of formula (I) with a dehydrohalogenation agent to produce a fluoroolefin, prefereably a C3 fluorolefin, more preferably a compound of formula (II), and even more preferably tetrafluoropropene.

In certain preferred embodiments, the present dehydrohalogenation step is carried out under conditions effective to provide a formula (I) conversion of at least about 40%, more preferably at least about 55%, and even more preferably at least about 70%. In certain preferred embodiments the conversion is at least about 90%, and more preferably about 100%. Further in certain preferred embodiments, the conversion of the compound of formula (I) to produce a compound of formula (II) is conducted under conditions effective to provide a formula (II) selectivity of at least about 25%, more preferably at least about 40%, more preferably at least about 70%, and even more preferably at least about 90%.

This reaction step can be carried out in the liquid phase or in the gas phase, or in a combination of gas and liquid phases, and it is contemplated that the reaction can be carried out batch wise, continuous, or a combination of these.

A. Liquid Phase Dehydrohalogenation

One preferred reaction step may be described, by way of illustration but not necessarily by way of limitation, by the following reaction equation in connection with embodiments in which the compound of formula (I) is 1,1,1,2,3 pentafluoropropane and the dehydrohalogenating agent is potassium hydroxide (KOH):

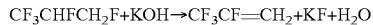

$$CF_3CHFCH_2F+KOH \rightarrow CF_3CF=CH_2+KF+H_2O$$

In such embodiments the KOH is preferably provided as an aqueous solution comprising from about 10% to about 50% by weight KOH, more preferably from about 20% to about 30% by weight.

In certain preferred embodiments, the KOH solution is brought to a relatively cool temperature, preferably from about −10° C. to about 10° C., preferably about 0° C. and introduced into a reaction vessel. The appropriate amount of formula (I) compound, which is preferably from about 1 to about 100 mole %, preferably, 0.9 to about 10 mole %, is then added to the reaction vessel. The reaction mixture is gradually heated, preferably with the addition of kinetic energy (agitation or stirring) to from about 40° C. to about 80° C., more preferably form about 50° C. to about 60° C. Since the preferred reaction is exothermic, the temperature of the reaction mixture may be allowed to increase to a temperature of from about 60° C. to about 95° C. more preferably form about 65° C. to about 75° C. The reaction pressure in such embodiments may vary, depending on particular processing parameters of each application, but in certain embodiments ranges from about 0 to about 200 psig during the course of the reaction. In certain embodiments the reaction the exothermic heat of reaction is removed (such as by cooling) from the reaction mixture so as to maintain the reaction temperature in the range first mentioned above. The overall reaction time in certain preferred embodiments is from about 5 to about 40 hours, more preferably from about 10 to abut 30 hours, and even more preferably for about 20 hours.

After the desired reaction time, the reaction mixture is preferably cooled to facilitate collection of the reaction product, for example to about 20° C. to about down to 40° C. Preferably, the conversion, and selectivity to HFO-1234, and preferably HFO-1234yf, are each at least about 90% and more preferably at least about 95%.

Another preferred reaction step may be described, by way of illustration but not necessarily by way of limitation, by the following reaction equation in connection with embodiments in which the compound of formula (I) is 1,1,1,3-tetrafluoro-2-chloropropane and the dehydrohalogenating agent is potassium hydroxide (KOH):

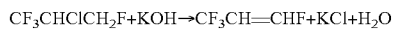

$$CF_3CHClCH_2F+KOH \rightarrow CF_3CH=CHF+KCl+H_2O$$

In such embodiments the KOH is preferably provided as an aqueous solution comprising from about 10% to about 50% by weight KOH, more preferably from about 15% to about 25% by weight, with or without Crown ether. The appropriate amount of formula (I) compound, which is preferably from about 5 to about 9 mole, is then added to the reaction vessel. The reaction mixture is gradually heated, preferably with the addition of kinetic energy (agitation or stirring) to from about 40° C. to about 80° C., more preferably form about 40° C. to about 60° C. at an overall reaction time of from about 2 to about 10 hours, more preferably from about 4 to abut 8 hours, and even more preferably for about 6 hours. After the designated reaction time, the reaction mixture is preferably cooled to facilitate collection of the reaction product, for example to about −70° C. Preferably, the conversion of the reaction is at least about 50%, more preferably at least about 60%, and even more preferably at least about 70%. The selectivity to HFO-1234ze is at least about 70%, more preferably at least about 75%, and even more preferably at least about 80%. Furthermore, in such embodiments it is preferred that of the HFO-1234ze produced, at least about 50%, more preferably at least about 75%, and even more preferably at least about 80% is trans-HFO-1234ze.

B. Gas Phase Dehydrohalogenation

Thus, it is contemplated that the dehydrohalogenation reaction step may be preformed using a wide variety of process parameters and process conditions in view of the overall teachings contained herein, such as for example the liquid phase reaction described above. However, it is preferred in certain embodiments that this reaction step comprise a gas phase reaction, preferably in the presence of catalyst, preferably a metal catalyst, and even more preferably one or more transition metal-based catalysts (including in certain preferred embodiments transition metal halide catalysts), such as $FeCl_3$, chromiumoxyfluoride, Ni (including Ni mesh), $NiCl_2$, $CrF_3$, and mixture thereof, supported or in bulk Other catalysts include carbon-supported catalysts, antimony-based catalysts (such as $Sb/Cl_5$), aluminum-based catalyst (such as $AlF_3$ and $Al_2O_3$). It is expected that many other catalysts may be used depending on the requirements of particular embodiments, including for example palladium-based catalyst, platinum-based catalysts, rhodium-based catalysts and ruthenium-based catalysts. Of course, two or more any of these catalysts, or other catalysts not named here, may be used in combination.

In general it is preferred that the catalysts are fluorinated. In preferred embodiments, fluorination of the catalysts comprises exposing the catalyst to a stream of HF at about reaction temperature and pressure. The gas phase dehydrohalogenation reaction may be conducted, for example, by introducing a gaseous form of a compound of formula (I) into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step is from about 150° C. to about 600° C., preferably about 200° C. to about 550° C., and even more preferably from about 300° C. to about 550° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum.

In certain embodiments, an inert diluent gas, such as nitrogen, may be used in combination with the compound of formula (I). When such a diluent is used, it is generally preferred that the compound of formula (I) comprise from about 5 to greater than 95% by weight based on the combined weight of diluent and formula (I) compound.

It is contemplated that the amount of catalyst use will vary depending on the particular parameters present in each embodiment. In preferred embodiments, the contact time, which is expressed as the ratio of the volume of the catalyst (ml) to the total feed flow (ml/sec) is from about 0.1 seconds to about 1000 seconds, and preferably from about 2 seconds to about 120 seconds.

One preferred dehydrohalogenation reaction comprises a dehydrofluorination reaction. For example, for embodiments in which the desired product of formula (II) is HFO-1234yf, it is preferred that the compound of formula (I) comprises 1,1,1,2,3 pentafluoropropane. Applicants have found that in such embodiments it is preferred to use as the catalyst a nickel-based catalyst, a carbon based catalyst, or a combination of these. In highly preferred embodiments the catalyst is preferably a nickel mesh catalyst or nickel on a carbon support. In such embodiments it is also generally preferred to introduce to the reactor HF gas and inert gas, such as nitrogen, in a formula (I):HF:Inert volume ratio of from about 100:20:20 to about 100:80:80, with a ratio of about 100:40:40 being even more preferred. In addition, it is generally preferred to conduct at least a substantial portion of the reaction at a temperature of from about 450° C. to about 600° C. In preferred aspects embodiments, the contact time is from about 0.1 seconds to about 1000 seconds, and preferably from about 2 seconds to about 10 seconds.

Preferably in such dehydrofluorination embodiments, the conversion is at least about 50%, more preferably at least about 65%, and even more preferably at least about 90%. Preferably, the selectivity to HFO-1234yf is at least about 70%, more preferably at least about 80% and more preferably at least about 90%.

Another preferred dehydrohalogenation reaction comprises a dehydrochlorination reaction. For example, for embodiments in which the desired product of formula (II) is HFO-1234ze, it is preferred that the compound of formula (I) comprises 1,1,1,3-tetrafluoro-2-chloropropane. Applicants have found that in certain embodiments it is preferred to use for this reaction a nickel-based catalyst at a reaction temperature of from about 200° C. to about 550° C., more preferably from about 250° C. to about 500° C., and even more preferably about 480° C. In certain other embodiments it is preferred to use for this reaction a activated carbon catalyst at a reaction temperature of from about 250° C. to about 550° C., more preferably from about 300° C. to about 550° C., and even more preferably about 515° C. In other embodiments it is preferred to use for this reaction a catalyst comprising 3% palladium on carbon at a reaction temperature of from about 400° C. to about 500° C., more preferably from about 425° C. to about 475° C., and even more preferably about 550° C. In yet other embodiments it is preferred to use for this reaction a catalyst comprising 2% nickel on carbon at a reaction temperature of from about 400° C. to about 500° C., more preferably from about 450° C. to about 500° C., and even more preferably about 485° C. In other embodiments it is preferred to use for this reaction a catalyst comprising chromiumoxyfluoride at a reaction temperature of from about 400° C. to about 500° C., more preferably from about 400° C. to about 450° C., and even more preferably about 435° C.

In such dehydrochlorination embodiments it is an option to introduce to the reactor inert gas, such as nitrogen, in a formula (I):inert volume ratio of from about 100:25 to about 100:75, with a ratio of about 100:50 being even more preferred.

In preferred aspects of the dehydrochlorination embodiments, the contact time is from about 0.1 to about 1000 seconds, and preferably from about 3 to about 120 seconds.

Preferably in such dehydrofluorination embodiments, the conversion is at least about 50%, more preferably at least about 65%, and even more preferably at least about 90%. Preferably, the selectivity to HFO-1234ze, and even more preferably to trans-HFO-1234ze, is at least about 70%, more preferably at least about 80% and more preferably at least about 90%.

In general the direction of flow of the gaseous components may is not critical, but in certain preferred embodiments the process flow is in the down direction through a bed of the catalyst. Preferably before each cycle of use, the catalyst is dried, pre-treated and activated. It may also be advantageous in certain embodiments to periodically regenerate the catalyst after prolonged use while in place in the reactor. Pre-treatment may include heating the catalyst to about 250° C. to about 430° C. with a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing nitrogen over the catalyst at temperatures of from about 100° C. to about 400° C. for from about 8 hours to about 3 days depending on the size of the reactor.

EXAMPLES

Certain features of the present invention are illustrated by the following examples, which should not be construed as limiting the claims in any way.

Examples 1-16

These examples illustrate gas phase dehydrofluorination of $CF_3CHFCH_2F$ (HFC-245eb) to $CF_3CF=CH_2$ (HFO-1234yf).

A 22-inch (½-inch diameter) Monel tube reactor is charged with 100 cc of catalyst, as specified in Table 1 below. A flow of 20 sccm of $N_2$ was maintained during the reaction. The reactor temperature is brought to the temperature indicated in the table. The HFC-245eb is passed through gas-flow controllers into a preheater maintained a temperature of about 300° C. The gas stream coming out of the preheater is passed through the catalyst bed at the desired temperature over a specified period of time. An on-line GC and a GCMS are used to analyze samples taken at the reactor exit line at regular time intervals. Finally, the reactor effluent is introduced into a 20% KOH scrubber solution at about room temperature to remove acid HF formed in-situ during the reaction. The effluent from the scrubber solution is then condensed to collect the products. The desired product $CF_3CF=CH_2$ (HFO-1234yf) is then isolated from the mixture by distillation.

The results are shown in Table 1 below.

TABLE 1

| $CF_3CHFCH_2F$ (HFC-245eb) → CF3CF=CH2 (1234yf) | | | | |
|---|---|---|---|---|
| Example#/Catalyst | T, ° C. | % Conversion of 245eb | % Selectivity to 1234yf | HFC-245eb, gm/hr |
| Example 1/ Ni-mesh | 495 | 36 | 100 | 10 |
| Example 2/ Ni-mesh | 525 | 67 | 100 | 10 |
| Example 3/ Ni-mesh | 565 | 89 | 78 | 10 |
| Example 4/ Ni on carbon | 495 | 63 | 94 | 10 |

TABLE 1-continued

CF$_3$CHFCH$_2$F (HFC-245eb) → CF3CF=CH2 (1234yf)

| Example#/Catalyst | T, °C. | % Conversion of 245eb | % Selectivity to 1234yf | HFC-245eb, gm/hr |
|---|---|---|---|---|
| Example 5/ Ni on carbon | 525 | 79 | 84 | 10 |
| Example 6/ Ni on carbon | 565 | 100 | 69 | 8 |
| Example 7/ Chromium Oxoxyfluoride | 420 | 69 | 47 | 11 |
| Example 8/ Chromium Oxoxyfluoride | 440 | 78 | 43 | 10 |
| Example 9/ Carbon | 500 | 32 | 96 | 10 |
| Example 10/ Carbon | 550 | 69 | 86 | 11 |
| Example 11/ Carbon | 600 | 85 | 76 | 12 |
| Example 12/ Pd/Carbon | 450 | 56 | 58 | 5 |
| Example 13/ Pd/Carbon | 475 | 68 | 53 | 7 |
| Example 15 4-6 wt % FeCl3/C | 250 | 42 | 49 | 8 |
| Example 16 4-6 wt % FeCl3/C | 300 | 59 | 37 | 8 |

Examples 17-21

These examples illustrate gas phase dehydrochlorination of CF$_3$CHClCH$_2$F to CF$_3$CH=CHF (HFO-1234ze).

A 22-inch (½-inch diameter) Monel tube reactor is charged with 50 cc of catalyst. A flow of 25 sccm of N2 is maintained during the reaction. The reactor temperature is brought to the temperature indicated in the Table 2 below. The CF$_3$CHClCH$_2$F is passed through gas-flow controllers into a preheater maintained a temperature of about 300° C. The gas stream coming out of the preheater is passed through the catalyst bed at the desired temperature. Finally, the reactor effluent is introduced into a 20% KOH scrubber solution at about room temperature to remove acid HF or HCl formed in-situ during the reaction. The effluent from the scrubber solution is then condensed to collect the products. The desired product CF$_3$CH=CHF (1234ze) is then isolated from the mixture by distillation. The reaction produced selectivity to CF$_3$CH=CHF of from about 80% to about 87%, and to trans-CF$_3$CH=CHF of from about 87% to about 92%.

TABLE 2

CF$_3$CHClCH$_2$F → CF$_3$CH=CHF (1234yf)

| Example#/Catalyst | T, °C. |
|---|---|
| Example 17/ Ni-mesh | 480 |
| Example 18/ activated carbon | 515 |
| Example 19/ Chromium Oxoxyfluoride | 436 |
| Example 20/ Pd/Carbon | 450 |
| Example 21 2% Ni on Carbon | 485 |

Example 22

This example illustrate liquid phase dehydrofluorination of CF$_3$CHFCH$_2$F (HFC-245eb) to CF$_3$CF=CH$_2$ (HFO-1234yf). The compound of formula (I) CF$_3$CHFCH$_2$F is stirred with 20% KOH solution in the presence or absence of 18-Crown ether at 50° C. to synthesize CF$_3$CF=CH$_2$. A cleaned and leak tested 2 gallon autoclave is evacuated and then 2.5 L KOH water solution is charged into it. The KOH solution was cooled down to 0° C. by a chiller. The autoclave is evacuated again and, using vacuum, 1.32 Kg CF$_3$CFHCFH$_2$ is then charged to it. The sealed reactor is gradually heated with stifling to 55° C. and then is heated by setting temperature at 55° C. After about 45 minutes reaction, the temperature increases to about 70° C. by exothermic reaction (pressure is 165 psig). A cooling liquid is then applied to the reactor bring the temperature down to 57° C. Then the reaction is continued at 55° C. for about 20 hours, and then the reaction mixture was cooled down to about 30° C. and the gas product was transferred into a cylinder at dry ice-acetone temperature. About 1.1 Kg of CF$_3$CF=CH$_2$ with GC purity of about 98.6% was collected.

Example 23

This example illustrates the liquid phase dehydrochlorination of CF$_3$CHClCH$_2$F to CF$_3$CH=CHF (HFO-1234ze). About 150 g of 20% KOH solution, 1 g of 18-Crown ether, and 10 g of CF$_3$CHClCH$_2$F are charged to a teflon-lined 300 ml autoclave. The mixture is stirred at 50° C. for 6 hours. The reaction progress is monitored by collecting samples and analyzing them by GC and MS in every 30 min. After the stipulated reaction period, the overhead gas mixture was transferred to a collection cylinder at −70° C. Analysis and overall material balance confirms that 72% of the starting CF$_3$CHClCH$_2$F is converted to CF$_3$CH=CHF (HFO-1234ze) and the product selectivity was 81%, selectivity of 89% with respect to the trans isomer.

Example 24

This example illustrates the addition of ClF to CF$_3$CH=CH$_2$ in a liquid phase reaction. Into a stirred tank 300 ml teflon-lined autoclave 10 g CF$_3$CH=CH$_2$ (0.104 mol) is charged. The reactor is subsequently cooled to −70° C. for ½ hour and 6.35 g of ClF (0.116 mol) is added slowly at a rate of 2 g/15 min. After addition of ClF, the reaction mixture is stirred at −55° C. for about 2 hours. Then the temperature is raised to 20° C. over a period of 1 hour under vigorous stirring. The mixture is stirred at this temperature for another 2 hours. The mixture is then cooled to −50° C., and 10 g of water are added to the reactor, and stirring continues for 15 additional minutes. The reactor temperature was then brought back to 20° C. The gaseous products from the reactor are then transferred to a collection cylinder which is maintained at liquid nitrogen temperature. GC and MS analysis and material balance of the sample from the collection cylinder show that almost 100% of the starting CF$_3$CH=CH$_2$ is converted to CF$_3$CFClCH$_2$F with almost 99% selectivity.

Example 25

This example illustrates the reaction of HF and Cl$_2$ with CF$_3$CH=CH$_2$ in a liquid phase reaction. It is an assumption that ClF is also generated in situ by the liquid phase reaction of HF and Cl$_2$ in the presence of transition metal halides such as FeCl$_3$, TaCl$_5$, TiCl$_4$, SbCl$_5$, SbCl$_3$, and CrCl$_3$, SbF$_3$, AlF$_3$, and $CrF_3$. In a first reaction vessel, HF, $Cl_2$ and metal chloride salts are stirred with $CF_3CH=CH_2$ at −40° C. for 2 hours to synthesize 48% $CF_3CHClCH_2F$ and 20% $CF_3CHClCH_2Cl$, 10% $CF_3CHClCH_2Cl$, 8% $CF_3CH_2CH_2F$, and 5% $CF_3CH_2CH_2Cl$ at a $CF_3CH=CH_2$ conversion level of 100%.

The same reaction is also performed using two autoclaves in two steps. In the first step, ClF is synthesized by the liquid phase reaction of HF and $Cl_2$ in the presence of transition metal halide such as $SbF_5$ in an autoclave which is then subsequently transferred to a second autoclave containing $CF_3CH=CH_2$ at about −40° C. Selectivity to $CF_3CHClCH_2F$ is about 80%.

Example 26

This example illustrates the addition of $F_2$ to $CF_3CH=CH_2$ in a liquid phase reaction. About 5-100 wt % $F_2$ in nitrogen is bubbled through 125 g of liquid trifluoropropylene (TFP) in a stirred Hastrelloy C reactor at about −20° C. to about −55° C. for about 1 hour in the presence of HF as the solvent. A 1 gallon Parr reactor is first charged with a relatively inert solvent, HF, to help with heat transfer and dilution of the organic. Then 125 grams of TFP is added batch wise to the reactor. The reaction mixture is continuously mixed and cooled to the desired temperature. Then the $F_2$ feed (10 wt %), diluted with $N_2$ (90 wt %), is introduced continuously directly into the reaction mixture through a dip tube until about 90% of the stoiciometric amount needed to convert all the TFP that is added. The reactor temperature and pressure are controlled automatically at the desired set points of between −20 to −55° C. and a constant pressure of 40 psig. The temperatures are chosen to minimize the amount of TFP that would exit the reactor with the $N_2$ diluent. The gases exiting the reactor are passed through a caustic scrubber carboy and an activated alumina column to remove acidity, then a dri-rite column to remove moisture, and finally the organic is collected in a DIT. When the desired amount of $F_2$ is added the reaction liquid is sampled. The sample is absorbed in $H_2O$ and the organic is recovered by phase separation. The organic is then analyzed by GC and GC/MS. The remaining material in the reactor is boiled off through the scrubbing system and the organic is collected in the DIT and analyzed by GC and GC/MS. The analyses are used to determine that the reaction has an overall selectivity to $CF_3CHFCH_2F$ of about 36-45%.

Example 27

This example illustrates addition of $F_2$ to $CF_3CH=CH_2$ in a gas phase reaction, which is illustrated by the following reaction scheme:

$$CF_3CH=CH_2 + F_2 \rightarrow CF_3CHFCH_2F$$

The same apparatus as described in Example 25 is used, except that gaseous TFP and 10% $F_2$ (90% dilution w/ $N_2$) are fed into the Parr reactor via a common dip tube. TFP is fed at a 50% stoichiometric excess. The reactor is kept at −18° C. and at atmospheric pressure. The reactor effluent is passed through a D1T, which collected most of the organic. Only a couple of grams of vapor are left in the Parr reactor at the end of the experiment. GC analysis of the material indicated about 10% conversion of the propylene. The selectivity to $CF_3CHFCH_2F$ is about 52% based on GC area percentage.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising converting at least one compound of formula (I):

$$CF_3CHXCH_2X \qquad (I)$$

to at least one compound of formula (II):

$$CF_3CZCHZ \qquad (II)$$

where X is independently Cl or F, and Z is independently is H or F, wherein at least a portion of said converting step is conducted in the liquid phase and in the presence of an aqueous solution of potassium hydroxide (KOH), and wherein said method further comprises forming said compound of formula (I) by halogen addition comprising contacting a fluorinated C3 olefin with a halogen addition agent under conditions effective to produce a compound of formula (I).

2. The method of claim 1 wherein said halogen addition agent comprises fluorine gas.

3. The method of claim 1 wherein said halogen addition agent comprises ClF.

4. The method of claim 3 wherein said halogen addition step comprises a liquid phase reaction.

5. The method of claim 1 wherein said halogen addition step is carried out at a temperature of from about −90° C. to about 50° C.

6. The method of claim 1 wherein said halogen addition agent comprises fluorine gas and a diluent.

7. The method of claim 1 wherein said fluorinated C3 olefin comprises a compound of formula (III)

$$CX_nY_{3-n}CY=CH_mY_{2-m} \qquad (III)$$

where each X is independently Cl or F, each Y is independently H, Cl or F, n is 1, 2 or 3, and m is 1 or 2.

8. The method of claim 7 wherein said compound of formula (III) comprises a compound of formula (IIIA)

$$CF_3CHCH_2 \qquad (IIIA).$$

9. The method of claim 8 wherein said compound of formula I comprises $$CF_3CHFCH_2F.$$

10. The method of claim 8 wherein said halogen addition agent is a compound of formula $X_mY_{2-m}$ where X, Y and m are as described above.

11. The method of claim 8 wherein said halogen addition agent is selected from the group consisting of ClF, $Cl_2$, $F_2$, HF and combinations of these.

12. The method of claim 10 wherein said halogen addition agent comprises $F_2$, said compound of formula (III) comprises 3,3,3-trifluoro-1-propene, and said compound of formula (I) comprises $CF_3CHFCH_2F$.

13. The method of claim 1 wherein said converting step comprises dehydrohalogenation of the compound of formula (I).

14. The method of claim 1 wherein said converting step comprises introducing said compound of formula (I) to a reaction system under conditions effective to convert at least about 50% of said compound of formula (I).

15. The method of claim 1 wherein said converting step comprises introducing said compound of formula (I) to a reaction system under conditions effective to produce a reaction product having at least about 70% selectivity to compound(s) of formula (II).

16. The method of claim 15 wherein said compound(s) of formula (II) include tetrafluoropropene.

17. The method of claim 15 wherein said compound(s) of formula (II) include HFO-1234yf.

18. The method of claim 15 wherein said compound of formula (I) is 1,1,1,2,3 pentafluoropropane.

19. The method of claim 18 wherein said compound of formula (II) comprises HFO-1234yf.

20. The method of claim 19 wherein said converting step is carried out under conditions effective to convert at least about 80% of said 1,1,1,2,3 pentafluoropropane and to provide a selectivity to HFO-1234yf of at least about 90%.

21. The method of claim 15 wherein said compound of formula (I) comprises 1,1,1,3-tetrafluoro-2-chloropropane and said compound of formula (II) comprises HFO-1234ze.

22. The method of claim 21 wherein said converting step is carried out under conditions effective to convert at least about 50% of said 1,1,1,3-tetrafluoro-2-chloropropane and to provide a selectivity to HFO-1234ze of at least about 70%.

23. A method of preparing fluorinated organic compounds comprising converting at least one compound of formula (I):

$$CF_3CHXCH_2X \qquad (I)$$

to at least one compound of formula (II):

$$CF_3CZCHZ \qquad (II)$$

where X is independently Cl or F, and Z is independently is H or F, wherein said method further comprises forming said compound of formula (I) by halogen addition comprising contacting a fluorinated C3 olefin with a halogen addition agent comprising $F_2$ wherein at least a portion of said contacting step is conducted in the gas phase under conditions effective to produce a compound of formula (I).

24. A method of preparing fluorinated organic compounds comprising converting at least one compound of formula (I):

$$CF_3CHXCH_2X \qquad (I)$$

to at least one compound of formula (II):

$$CF_3CZCHZ \qquad (II)$$

where X is independently Cl or F, and Z is independently is H or F, and wherein said at least one compound of formula II comprises HFO-1234ze, wherein at least a portion of said converting step is conducted in the liquid phase, and wherein said method further comprises forming said compound of formula (I) by halogen addition comprising contact a fluorinated C3 olefin with a halogen addition agent under conditions effective to produce a compound of formula (I).

* * * * *